United States Patent
Putz

(10) Patent No.: US 8,977,335 B2
(45) Date of Patent: Mar. 10, 2015

(54) INTRACRANIAL SENSING AND MONITORING DEVICE WITH MACRO AND MICRO ELECTRODES

(75) Inventor: David A. Putz, Pewaukee, WI (US)

(73) Assignee: Ad-Tech Medical Instrument Corp., Racine, WI (US)

( * ) Notice: Subject to any disclaimer, the term of this patent is extended or adjusted under 35 U.S.C. 154(b) by 414 days.

(21) Appl. No.: 13/434,300

(22) Filed: Mar. 29, 2012

(65) Prior Publication Data

US 2013/0261489 A1    Oct. 3, 2013

(51) Int. Cl.
*A61B 5/0478*    (2006.01)

(52) U.S. Cl.
USPC .......................................... 600/378; 600/383

(58) Field of Classification Search
CPC .................................................... A61B 18/0478
USPC ................................... 600/383, 544, 378.383
See application file for complete search history.

(56) References Cited

U.S. PATENT DOCUMENTS

| | | | |
|---|---|---|---|
| 4,735,208 A | 4/1988 | Wyler et al. | |
| 4,805,625 A | 2/1989 | Wyler | |
| 4,869,255 A * | 9/1989 | Putz | 600/378 |
| 4,903,702 A | 2/1990 | Putz | |
| 5,044,368 A | 9/1991 | Putz | |
| 5,097,835 A | 3/1992 | Putz | |
| 5,237,995 A * | 8/1993 | Cano | 600/396 |
| 6,011,996 A | 1/2000 | Gielen et al. | |
| 7,006,859 B1 * | 2/2006 | Osorio et al. | 600/378 |
| 7,221,981 B2 * | 5/2007 | Gliner | 607/116 |
| 7,536,215 B2 | 5/2009 | Putz et al. | |
| 7,551,951 B1 * | 6/2009 | Osorio et al. | 600/378 |
| 7,945,333 B2 | 5/2011 | Gilner et al. | |
| 8,352,012 B2 * | 1/2013 | Besio | 600/388 |
| 8,774,937 B2 * | 7/2014 | Mercanzini et al. | 607/116 |
| 2001/0014820 A1 | 8/2001 | Gielen et al. | |
| 2001/0016765 A1 | 8/2001 | Gielen et al. | |
| 2002/0022872 A1 | 2/2002 | Gielen et al. | |
| 2004/0199237 A1 * | 10/2004 | Mills et al. | 607/152 |
| 2005/0154424 A1 | 7/2005 | Tass et al. | |
| 2006/0265039 A1 | 11/2006 | Bartic et al. | |
| 2009/0276005 A1 | 11/2009 | Pless | |
| 2011/0154655 A1 | 6/2011 | Hetke et al. | |
| 2013/0144365 A1 * | 6/2013 | Kipke et al. | 607/93 |

FOREIGN PATENT DOCUMENTS

WO    WO2011067297 A1    6/2011

* cited by examiner

*Primary Examiner* — Lee S Cohen
(74) *Attorney, Agent, or Firm* — Jansson Munger McKinley & Shape Ltd.

(57) ABSTRACT

A cortical sensing device for contact with the surface of the brain is provided that includes a support member, at least one macroelectrode sensing element secured with respect to the support member and at least one microelectrode sensing element secured with respect to the macroelectrode. The support member is substantially thin and made from flexibly-conformable material to accurately and safely place the sensing device upon the brain surface. The microelectrode sensing element is surrounded by the macroelectrode brain-contact surface of the macroelectrode sensing element. The first surface of the support member, the macroelectrode brain-contact surface and the microelectrode brain-contact surface are substantially co-planar to abut the surface of the brain for sensing and monitoring.

15 Claims, 7 Drawing Sheets

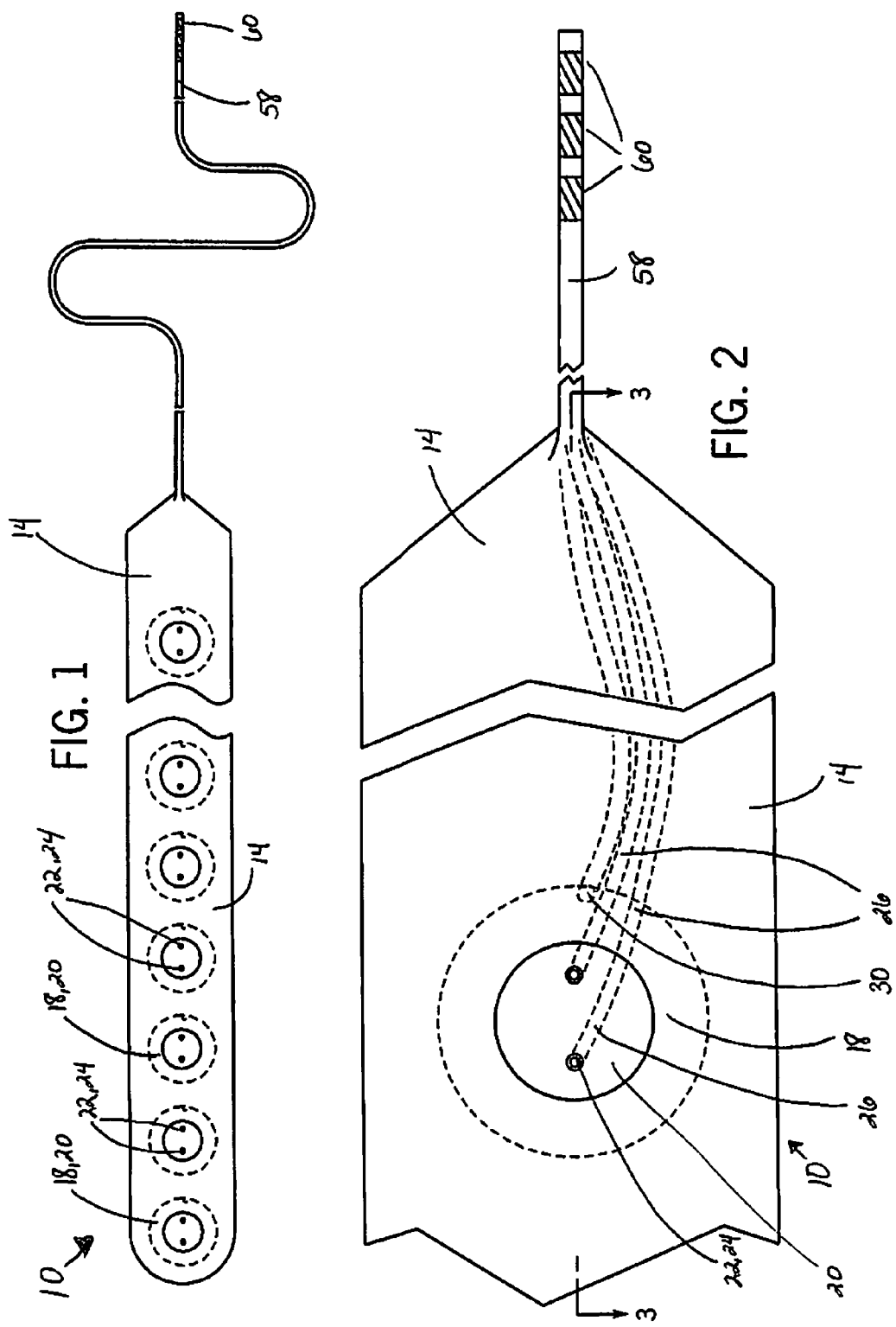

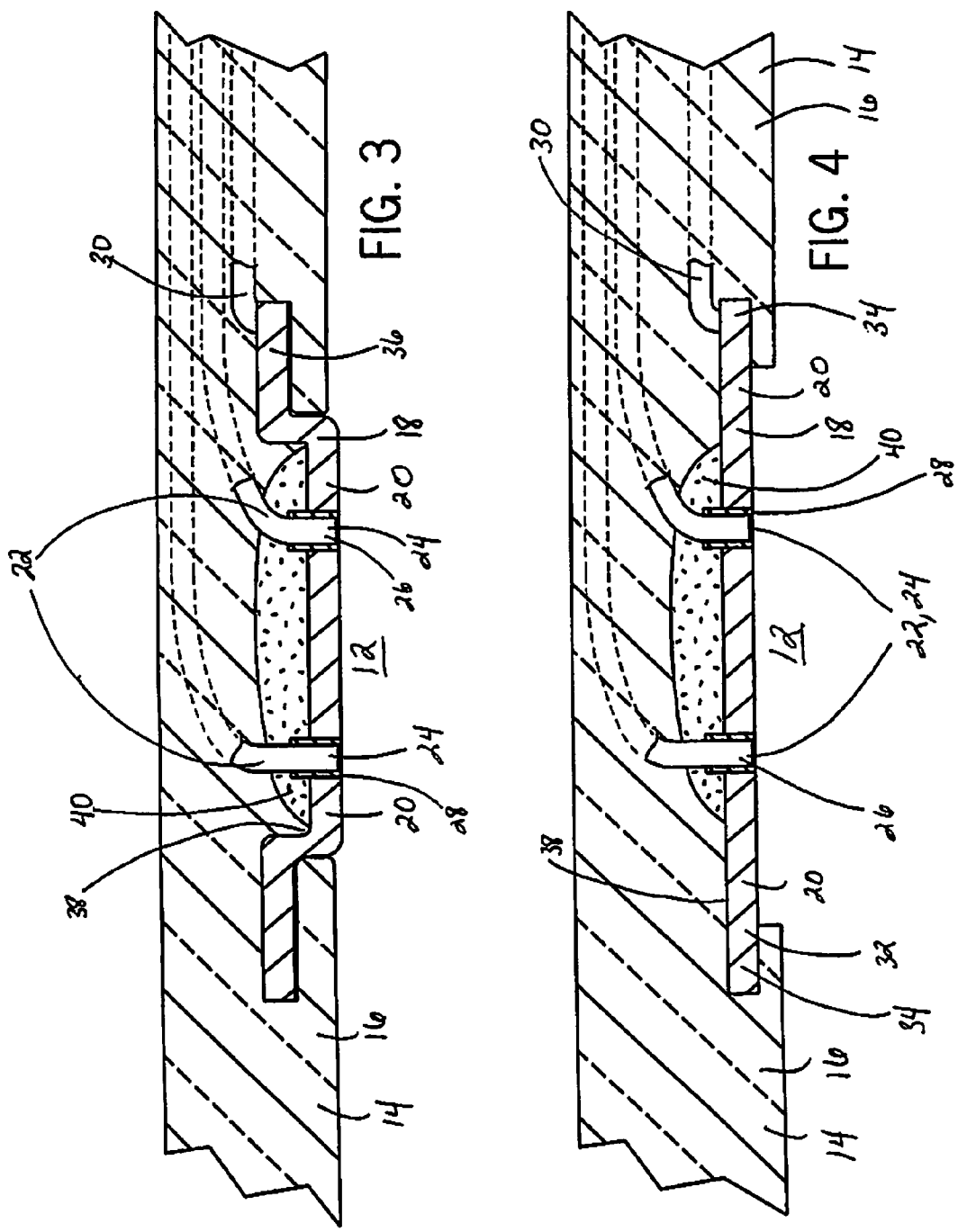

INTRACRANIAL SENSING AND MONITORING DEVICE WITH MACRO AND MICRO ELECTRODES

FIELD OF THE INVENTION

This invention is related generally to intracranial sensing devices and, more particularly, to strip/grid and depth electrode sensing devices.

BACKGROUND OF THE INVENTION

Monitoring and surgical removal of epileptogenic brain is indicated for the treatment of many medically refractory focal seizure disorders. Such surgery demands a high degree of accuracy in identifying the epileptogenic foci. Various methods have been used in attempting to determine the location of these foci, and all involve sensing cortical electrical activity using electrical contacts applied in various ways.

While scalp contacts were customarily used for many years to identify epileptogenic foci, accurate localization of the foci was usually very difficult with the recordings obtained from such contacts. Therefore, it has become customary for medical centers to use intracranial recording techniques to better define regions of cortical epileptogenicity whereby the safety and effectiveness of epileptogenic brain monitoring and removal is enhanced.

Intracranial recording techniques have typically involved one of two different types of sensing devices—intracortical depth electrodes or cortical strip/grid electrodes. Depth electrodes are necessary in certain circumstances and applications. Techniques using cortical strip/grid electrodes have been shown to be relatively safe and serve as an alternative to depth electrodes.

Cortical strip/grid electrodes are not invasive of brain tissue. Depth electrodes are narrow, typically cylindrical dielectric structures with contact bands spaced along their lengths. Such electrodes are inserted into the brain in order to establish good electrical contact with different portions within the brain. Cortical strip/grid electrodes, on the other hand, are flat strips that support contacts spaced along their lengths. Such strip/grid electrodes are inserted between the dura and the brain, along the surface of and in contact with the brain, but not within the brain.

Examples of such electrodes include but are not limited to electrodes described in U.S. Pat. No. 4,735,208 (Wyler, et al.), U.S. Pat. No. 4,805,625 (Putz), U.S. Pat. No. 4,903,702 (Putz), U.S. Pat. No. 5,044,368 (Putz), and U.S. Pat. No. 5,097,835 (Putz).

A cortical strip/grid electrode has a flexible dielectric strip within which a plurality of spaced aligned flat contacts and their lead wires are enclosed and supported in place between front and back layers of the material forming the dielectric strip. Each flat contact has a face or main contact surface which is exposed by an opening in the front layer of the dielectric strip. Insulated lead wires, one for each contact, are secured within the strip and exit the strip from a proximal end. The dielectric material used in such cortical strip/grid electrodes is typically a flexible, bio-compatible material such as silicone.

While the "typical" cortical strip/grid electrode works fine in many situations, there are applications for which its structure is not well suited. For instance, it may be desirable to sense and record both cellular activity within the brain with a microelectrode while simultaneously monitoring/recording standard electroencephalography (EEG) activity of the brain with a macroelectrode. Cortical sensing devices that allow sensing elements such as electrical contacts to simultaneously sense/record both cellular and EEG activity in an easy and safe manner would be an improvement over the current state of the art.

OBJECTS OF THE INVENTION

It is an object of the invention to provide an improved cortical sensing device that simultaneously monitors/records both cellular and EEG activity in an easy and safe manner.

Another object of the invention is to provide a cortical sensing device that is easy to place at a desired position on the brain surface.

Another object of the invention is to provide a cortical sensing device that anchors itself to the brain surface so as to prevent unintentional movement of the sensing device with respect to the brain surface.

Another object of the invention is to provide a cortical sensing device that provides a large surface area contacting the brain.

Another object of the invention to provide a method of accurately positioning a cortical sensing device upon the brain surface.

These and other objects of the invention will be apparent from the following descriptions and from the drawings.

SUMMARY OF THE INVENTION

The invention is for an improved cortical sensing device for contact with the surface of the brain at a desired position on a brain surface. The sensing device includes a support member of a flexibly-conformable material and having a first surface. The support member is substantially thin and made from material that is flexibly-conformable. Flexibly-conformable refers to the ability of the support member to easily conform to the contours of the brain surface where the sensing device is placed while being able to recover its original shape and size when removed. The sensing device also includes at least one macroelectrode sensing element secured with respect to the support member and having a macroelectrode brain-contact surface as well as at least one microelectrode sensing element secured with respect to the macroelectrode and having a microelectrode brain-contact surface surrounded by the macroelectrode brain-contact surface. The first surface, the macroelectrode brain-contact surface and the microelectrode brain-contact surface are substantially co-planar to abut the surface of the brain for sensing and monitoring.

In certain preferred embodiments, the microelectrode sensing element is a micro-wire insulated therealong to the microelectrode brain-contact surface with a bio-compatible material to prevent electrical interaction between the microelectrode sensing element and macroelectrode sensing element. Also preferred is that the macroelectrode sensing element includes a lead wire extending from it. A highly preferred embodiment finds the lead wire and the micro-wire being imbedded in and extending along the support member to exit therefrom for remote electrical connection.

Most preferred is that the microelectrode sensing element is adapted to monitor cellular neuron activity signals within the brain, while the macroelectrode sensing element is adapted to monitor EEG brain activity signals from the brain.

A highly preferred embodiment includes the macroelectrode sensing element being a flat member which has peripheral portions engaged by the support member. Another highly preferred embodiment includes the macroelectrode sensing element having a recessed flange thereabout engaged by the support member such that the macroelectrode brain-contact surface is substantially co-planar with the first surface of the support member.

It is preferred that the macroelectrode sensing element has a rear surface opposite the macroelectrode brain-contact surface with bio-compatible epoxy thereon further securing the microelectrode sensing element to the macroelectrode sensing element. More desirable is that the support member be formed from a dielectric, bio-compatible material, most preferably a medical or implant grade silicone, polyurethane or other biocompatible elastomer.

A highly desirable embodiment includes a plurality of microelectrode sensing elements spaced from one another on the macroelectrode sensing element. Also highly preferred is that the support member is an elongate strip or grid array having a plurality of macroelectrode sensing elements therealong, each having at least one of the microelectrode sensing element. Preferably the support member includes a center portion which has the macroelectrode sensing element and its related microelectrode sensing element(s) and has a peripheral portion and a plurality of flexible pads thereabout. Preferably each pad is located along the peripheral portion and has its own center, the plurality of pads are positioned such that the centers are not collinear. The flexible pads facilitate engagement of the sensing device with brain surface. In this manner, the sensing device is substantially clover-shaped.

Most desirable is that the macroelectrode sensing element be comprised of a single layer of material having a thickness of about 0.0005-0.004 inches and a diameter of about 1.0 mm.-10.0 mm. Also desirable is that the material is stainless steel or a noble alloy selected from the group consisting of platinum, gold, palladium, iridium and ruthenium alloys and combinations thereof.

It is desirable that the microelectode brain-contact surface has a diameter of about 10-250 microns. Also desirable is that the microelectrode sensing element be comprised of a noble alloy selected from the group consisting of platinum, gold, palladium, iridium and ruthenium alloys and combinations thereof.

Another highly preferred embodiment for a sensing device for contact with brain tissue includes a flexible support sleeve having an outer surface and inner surface defining a cavity. The highly preferred embodiment also includes at least one macroelectrode sensing element secured with respect to the outer surface and having a macroelectrode brain-contact surface as well as a lead wire secured to each macroelectrode sensing element and extending into and along the cavity. The highly preferred embodiment further includes at least one microelectrode sensing element secured with respect to the macroelectrode sensing element and having a microelectrode brain-contact surface surrounded by the macroelectrode brain-contact surface as well as a micro-wire secured to each macroelectrode sensing element and extending into and along the cavity. It is most preferred that the macroelectrode brain-contact surface and the microelectrode brain-contact surface are in substantially the same curved surface to abut brain tissue for sensoring and monitoring.

The sensing device includes the features as described above, and also includes a linear-array plural-contact tail on the end of the electrode which is not implanted in the brain (this is the end distal from the macroelectrode sensing element and microelectrode sensing element). In highly preferred embodiments, the plural contacts of the plural-contact tail are annular sleeves having necked-in (e.g., crimped) ends. This configuration of a plural-contact tail allows connection with a medical connector and monitoring device remote from the patient.

Other objects, advantages and features will become apparent from the following specification when taken in conjunction with the accompanying drawings.

BRIEF DESCRIPTION OF THE DRAWINGS

FIG. 1 is a top view of a cortical sensing device shown in the grid/strip electrode embodiment, in accordance with this invention.

FIG. 2 is a close-up view of the sensing device of FIG. 1, showing the lead wire and micro-wires as well as the plural-contact tail.

FIG. 3 is a cross-sectional view of the cortical sensing device taken substantially along line 3-3 of FIG. 2.

FIG. 4 is a cross-sectional view of the cortical sensing device of FIG. 1, showing the macroelectrode sensing element as a flat member.

DETAILED DESCRIPTION OF PREFERRED EMBODIMENTS

Figure 5:
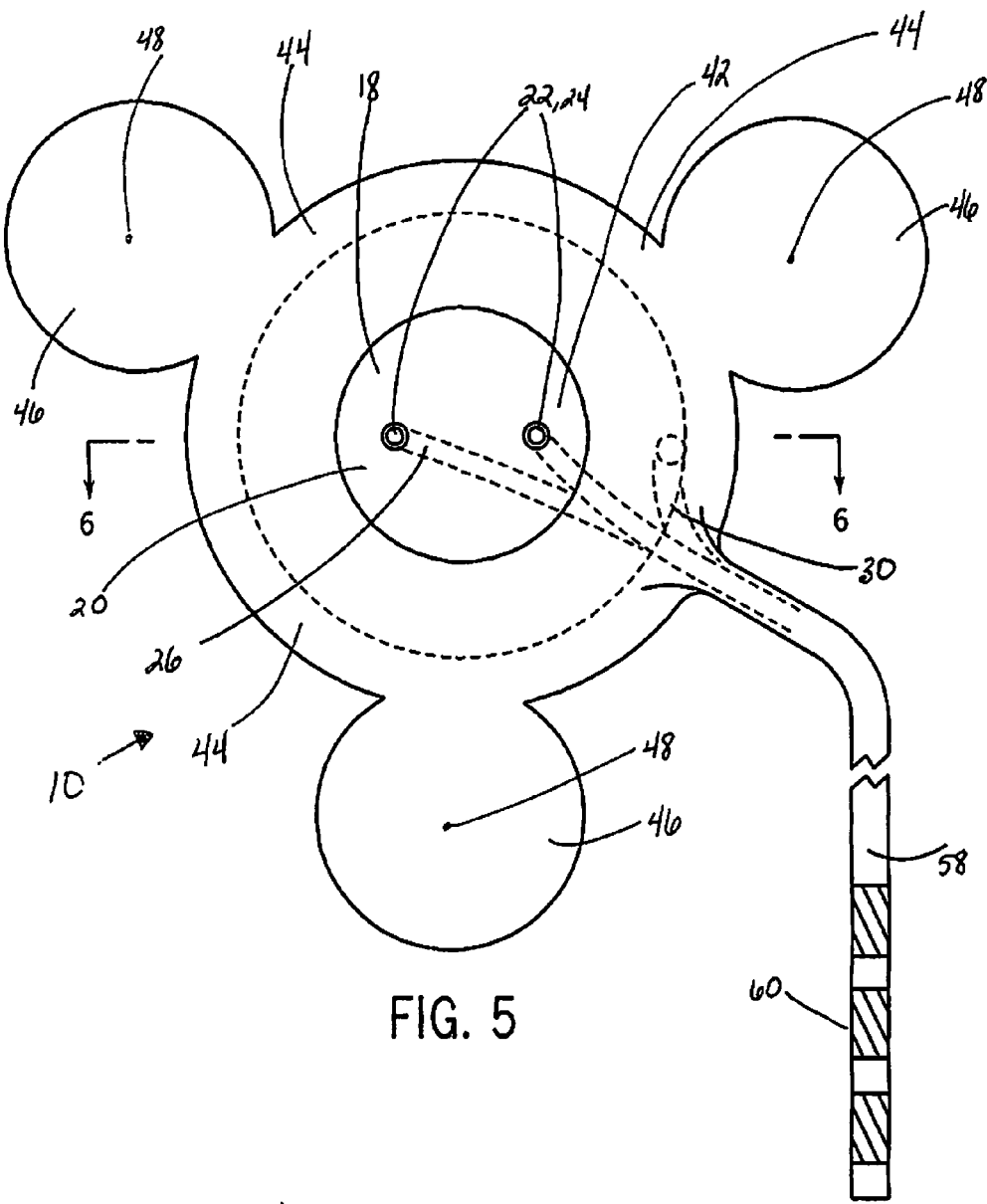
FIG. 5 is a top view of an embodiment of the sensing device of FIG. 1, illustrating the pads.

FIGS. 1-2 are top views of a cortical sensing device 10 having a preferred embodiment in accordance with this invention. Cortical sensing device 10 includes a support member 14 made of a flexibly-conformable material. Support member 14 has a first surface 16 for contact with a surface of the brain 12. Device 10 also includes at least one macroelectrode sensing element 18 secured with respect to support member 14. Macroelectrode sensing element 18 has a macroelectrode brain-contact surface 20. Device 10 includes at least one microelectrode sensing element 22 which is secured with respect to macroelectrode 18 and has a microelectrode brain-contact surface 24 surrounded by macroelectrode brain-contact surface 20. First surface 16, macroelectrode brain-contact surface 20 and microelectrode brain-contact surface 24 are substantially co-planar to abut the surface of brain 12 for sensoring and monitoring. FIGS. 1-2 illustrate sensing device 10 as a grid/strip electrode.

FIGS. 3-4 illustrate that microelectrode sensing element 22 is a micro-wire 26 which is insulated along its length up to microelectrode brain-contact surface 24. Micro-wire 26 is insulated with a bio-compatible material 28 to prevent electrical interaction between microelectrode sensing element 22 and macroelectrode sensing element 18. It is important to note that each macroelectrode sensing element 18 can have one or more microelectrode sensing elements 22. By way of example only, FIGS. 1-11 illustrate two microelectrode sensing elements 22 for each macroelectrode sensing elements 18.

FIGS. 3-4 also illustrate that a lead wire 30 extends from macroelectrode sensing element 18. Lead wire 30 and microwire(s) 26 are imbedded in and extend along support member 14 to exit therefrom for remote electrical connection as shown in FIGS. 2 and 5. Microelectrode sensing element 22 is adapted to monitor cellular neuron activity signals within the brain, while macroelectrode sensing element 18 is adapted to monitor EEG brain activity signals from the brain. Microelectrode sensing element 22 operates at a higher frequency than macroelectrode sensing element 18.

Figure 6:
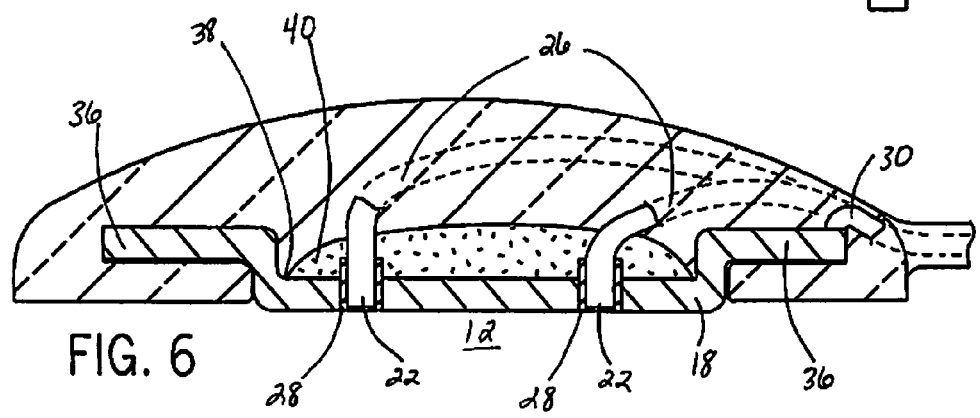
FIG. 6 is a cross-sectional view of the cortical sensing device taken substantially along line 6-6 of FIG. 5.
Figure 7:
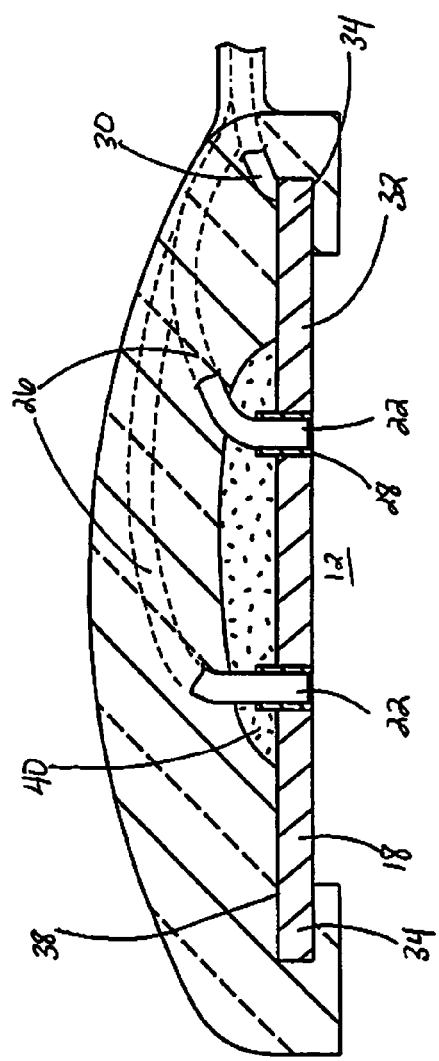
FIG. 7 is a cross-sectional view of the cortical sensing device of FIG. 1, showing the macroelectrode sensing element as a flat member.

Macroelectrode sensing element 18 can be a flat member with peripheral portions 34 engaged by support member 14 as shown in FIGS. 4 and 7. Macroelectrode sensing element 18 can also have a recessed flange 36 which engages support member 14 such that macroelectrode brain-contact surface 20 is substantially co-planar with first surface 16 of support member 14 as seen in FIGS. 3 and 6. Both the flat member and recessed flange 36 configurations of macroelectrode sensing elements 18 have a diameter of 1.0 to 10.0 mm that is exposed to surface of brain 12.

FIGS. 3-4 and 6-7 illustrate that macroelectrode sensing element 18 has a rear surface 38 opposite macroelectrode brain-contact surface 20. Rear surface 38 has bio-compatible epoxy 40 thereon to further secure microelectrode sensing element 22 to macroelectrode sensing element 18. Microelectrode sensing element 22 and macroelectrode sensing element 18 are also secured through frictional engagement.

Support member 14 is preferably of a medical or implant grade silicone, polyurethane or other biocompatible elastomer. Support member 14 is formed from a single thin and substantially planar layer of a dielectric material that is both flexible and bio-compatible (see FIGS. 1-2). A silicone material such as a medical grade of SILASTIC® is preferred although an equivalent dielectric elastomer can also be used. The material is also preferably transparent to enable the underlying features of the cortical surface to be visualized when sensing device 10 is placed upon the brain.

FIG. 1 shows that device 10 can include one or a plurality of microelectrode sensing elements 22 spaced from one another on macroelectrode sensing element 18. Support member 14 can be an elongate strip or grid array which has a plurality of macroelectrode sensing elements 18 therealong, each having at least one or many microelectrode sensing elements 22 as seen in FIGS. 1-2.

Cortical sensing device 10 is also provided with three substantially similar circular pads 46 extending outward from support member 14 as illustrated in FIG. 5. FIG. 5 illustrates that support member 14 has a center portion 42 which includes macroelectrode sensing element 18 and its related microelectrode sensing element(s) 22. Center portion 42 has a peripheral portion 44. A plurality of flexible pads 46 surround peripheral portion 44, each pad 46 being located along peripheral portion 44 and having its own center 48. The plurality of pads 46 are positioned such that the centers 48 are not collinear. Flexible pads 46 facilitate engagement of sensing device 10 with the brain surface. Pads 46 interact with brain surface 12 so that sensing device 10 clings to the cortex. Lateral movement of sensing device 10 is avoided once device 10 has been individually positioned at a desired specific location that is selected by the physician for that device 10 to perform a certain procedure such as sensing brain activity.

As illustrated best in FIGS. 1-2 and 5, macroelectrode sensing element 18 is comprised of a single layer of material having a thickness of about 0.0005-0.004 inches and a diameter of about 1.0 mm.-10.0 mm. Microelectode brain-contact surface 24 preferably has a diameter of about 10-250 microns.

The thickness and diameter of support member 14 are substantially uniform throughout the strip, preferably about 0.006 in. In the support member 14 embodiment with pads 46, the center 48 of each pad 46 is equidistant from the centers of the other two pads 46, thereby forming a clover-like shape. Each pad 46 is attached to support member 14 along an arc as seen in FIG. 5.

Pads 46 do not need to be sandwiched between the dura and the cortex to remain in place. Moreover, given the size and shape of sensing device 10, one can clearly understand that the weight of sensing device 10 is less of a factor in its ability to stay in one spot than is the case for the heavier strip sensing devices in the prior art.

The thinness of pads 46, the length of arcs, and the nature of the material selected for support member 14 each contribute to the ability of pads 46 to retain their shape but still be sufficiently flexible to conform to an area of brain surface 12 of comparable size.

Macroelectrode sensing element 18 and microelectrode sensing element 22 are preferably constructed from a noble alloy such as platinum, gold, palladium, iridium and ruthenium alloys and combinations thereof. Macroelectrode sensing element 18 can be also constructed of stainless steel.

Figure 8:
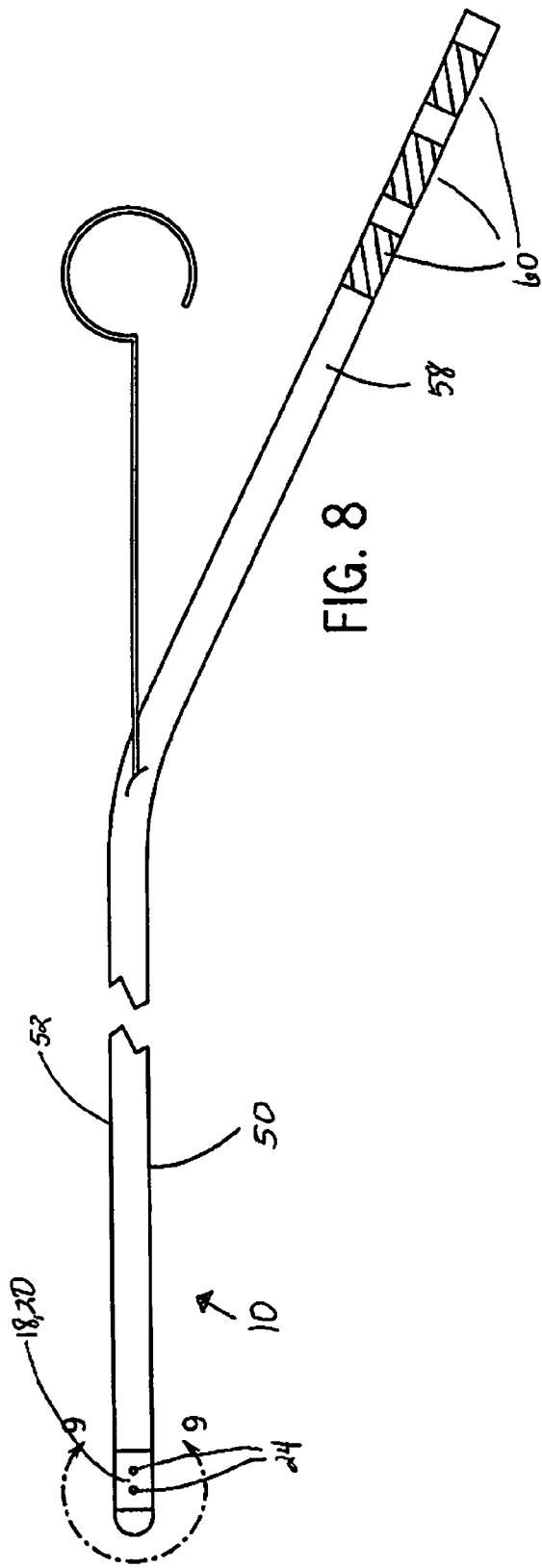
FIG. 8 is a perspective view of an alternative embodiment of the sensing device of FIG. 1, illustrating the flexible support sleeve.
Figure 9:
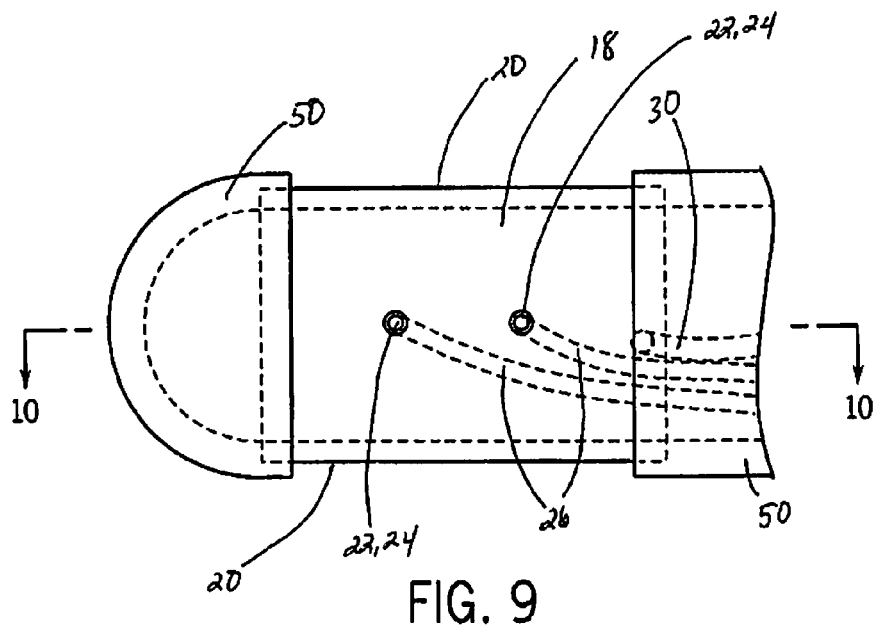
FIG. 9 is a cross-sectional view of the sensing device taken substantially along line 9-9 of FIG. 8.
Figure 10:
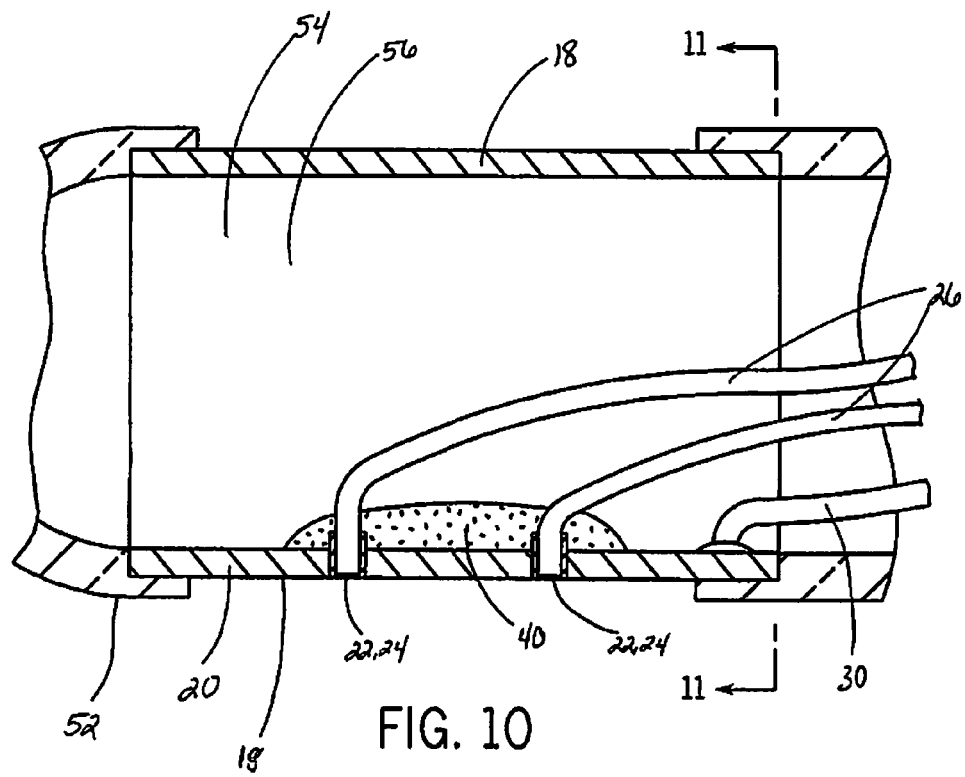
FIG. 10 is a cross-sectional view of the sensing device taken substantially along line 10-10 of FIG. 9.
Figure 11:
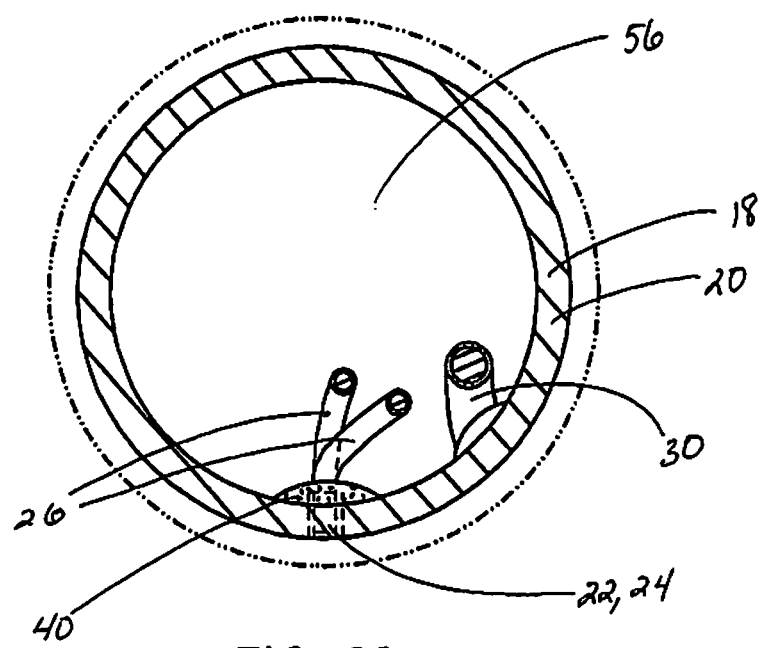
FIG. 11 is a cross-sectional view of the sensing device taken substantially along line 11-11 of FIG. 10.
Figure 12:
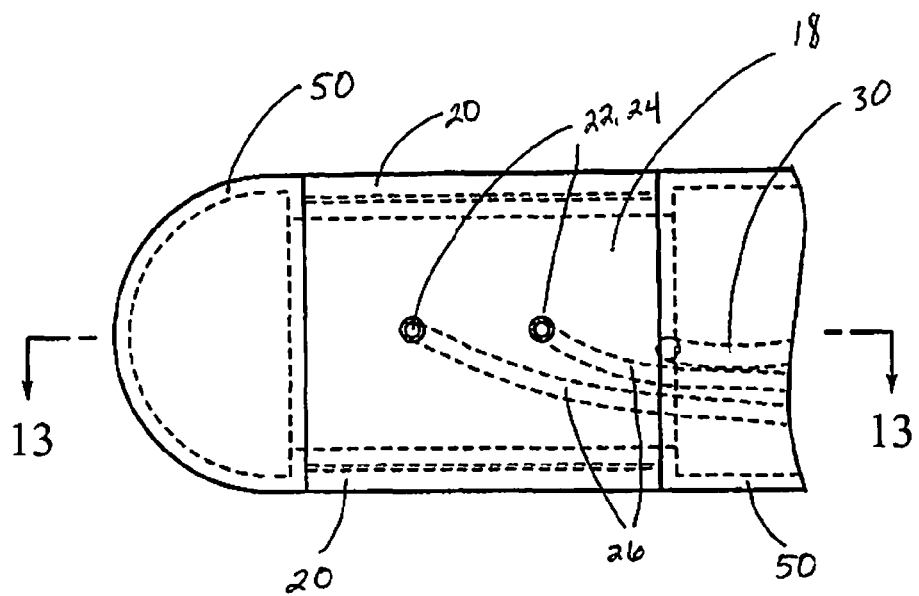
FIG. 12 is a cross-sectional view of the sensing device of FIG. 8.
Figure 13:
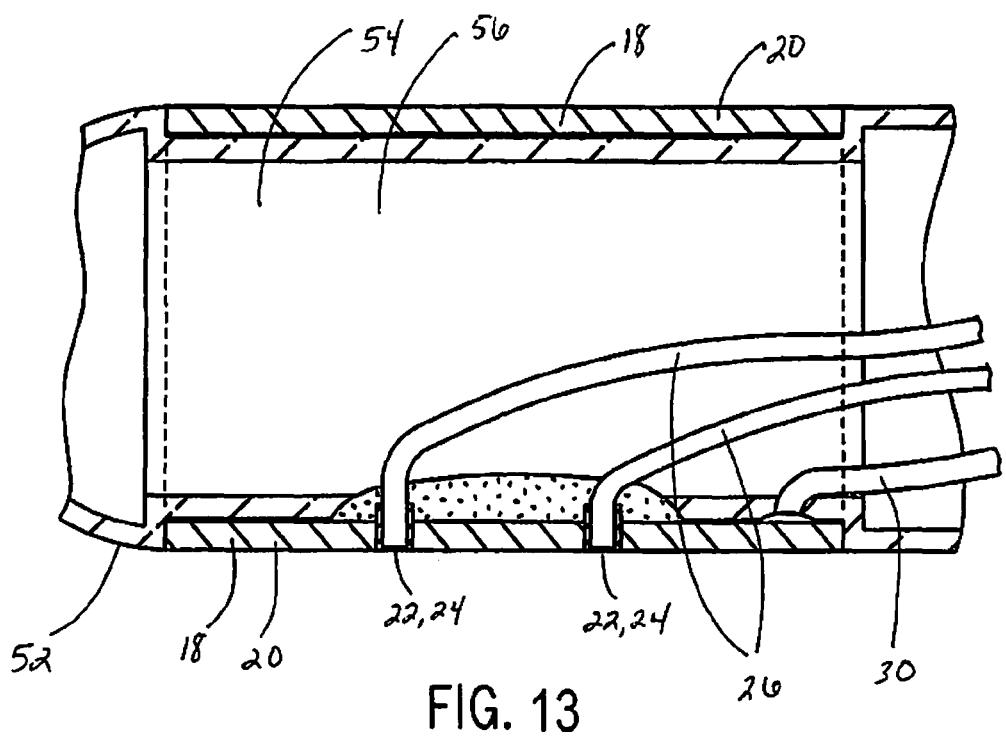
FIG. 13 is a cross-sectional view of the sensing device taken substantially along line 13-13 of FIG. 12.

As seen in FIGS. 8-11, another embodiment of device 10 is commonly referred to as a depth electrode for contact with brain tissue. In this embodiment device 10 includes a flexible support sleeve 50 as seen best in FIG. 8. Support sleeve 50 has an outer surface 52 and an inner surface 54 which define cavity 56 as illustrated in FIG. 10. Preferably, support sleeve 50 is constructed of a one-piece body so as to be a seamless component as illustrated in FIGS. 12-13. Macroelectrode sensing element 18 is preferably flush with support sleeve 50, however, an alternative embodiment is to have macroelectrode sensing element 18 slightly recessed inward from support sleeve 50 as seen in FIGS. 9-10 and 12-13.

In this embodiment, at least one macroelectrode sensing element 18 is secured with respect to outer surface 52 and has a macroelectrode brain-contact surface 20 as illustrated in FIGS. 9-10. Lead wire 30 is secured to each macroelectrode sensing element 18 and extends into and along cavity 56 as shown in FIGS. 10-11. At least one microelectrode sensing element 22 is secured with respect to macroelectrode sensing element 18 and microelectrode sensing element 22 includes a microelectrode brain-contact surface 24 surrounded by macroelectrode brain-contact surface 20. This embodiment also includes a micro-wire 26 secured to each macroelectrode sensing element 18 as seen best in FIG. 10. Micro-wire 26 extends into and along cavity 56. Macroelectrode brain-contact surface 20 and microelectrode brain-contact surface 24 are in substantially the same curved surface to abut brain tissue 12 for sensoring and monitoring. In this embodiment, macroelectrode sensing element 18 is comprised of a single layer of material having a thickness of about 0.0005-0.004 inches and a diameter of about 0.3 mm.-5.0 mm.

Device 10, whether in a strip/grid configuration or depth electrode configuration, typically includes a linear-array plural-contact tail 58 on the end of device 10 which is not implanted in the brain (this is the end distal from the macroelectrode sensing element 18 and microelectrode sensing element 22) as shown in FIGS. 1-2 and 8. Plural contacts 60 of plural-contact tail 58 are annular sleeves having necked-in (e.g., crimped) ends. This configuration of a plural-contact tail 58 allows connection with a medical connector and external monitoring device remote from the patient. Where device 10 is intended to monitor electrical brain activity, external monitoring device will preferably consist of a conventional monitoring device with output display and a suitable power source to record or display information communicated by sensing device 10.

Device 10 is also provided with numerical indicia (not shown) to use to distinguish one device 10 from the others as numerous devices 10 may be used at one time. The numerical indicia allows individual users to more quickly, easily and with greater assurance associate each device 10 with a corresponding external device Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A cortical sensing device for contact with the surface of the brain comprising:
    a support member of a flexibly-conformable material and having a first surface;
    at least one macroelectrode sensing element secured with respect to the support member and having a macroelectrode brain-contact surface;
    at least one microelectrode sensing element secured with respect to the macroelectrode and having a microelectrode brain-contact surface surrounded by the macroelectrode brain-contact surface, wherein the first surface, the macroelectrode brain-contact surface and the microelectrode brain-contact surface are substantially co-planar to abut the surface of the brain for monitoring, the microelectrode sensing element is a micro-wire insulated therealong to the microelectrode brain-contact surface with a bio-compatible material to prevent electrical interaction between the microelectrode sensing element and macroelectrode sensing element.

2. The sensing device of claim 1 further including a lead wire extending from the macroelectrode sensing element, the lead wire and the micro-wire being imbedded in and extending along the support member to exit therefrom for remote electrical connection.

3. The sensing device of claim 1 wherein the microelectrode sensing element is adapted to monitor cellular neuron activity signals within the brain, while the macroelectrode sensing element is adapted to monitor EEG brain activity signals from the brain.

4. The sensing device of claim 1 wherein the macroelectrode sensing element is a flat member and has peripheral portions engaged by the support member.

5. The sensing device of claim 1 wherein the macroelectrode sensing element has a recessed flange thereabout engaged by the support member such that the macroelectrode brain-contact surface is substantially co-planar with the first surface of the support member.

6. The sensing device of claim 1 wherein the macroelectrode sensing element has a rear surface opposite the macroelectrode brain-contact surface with bio-compatible epoxy thereon further securing the microelectrode sensing element to the macroelectrode sensing element.

7. The sensing device of claim 1 wherein the support member is formed from a dielectric, bio-compatible material.

8. The sensing device of claim 1 wherein the support member is of a medical or implant grade silicone, polyurethane or other biocompatible elastomer.

9. The sensing device of claim 1 further including a plurality of the microelectrode sensing elements surrounded by the macroelectrode sensing element.

10. The sensing device of claim 1 wherein the support member is an elongate strip or grid array having a plurality of macroelectrode sensing elements therealong, each having at least one of the microelectrode sensing element.

11. The sensing device of claim 1 wherein the support member comprises:
    a center portion which includes the macroelectrode sensing element and its related microelectrode sensing element(s) and has a peripheral portion;
    a plurality of flexible pads thereabout, each pad located along the peripheral portion and having its own center, the plurality of pads being positioned such that the centers are not collinear,
whereby the flexible pads facilitate engagement of the sensing device with brain surface.

12. The sensing device of claim 1 wherein the macroelectrode sensing element is comprised of a single layer of material having a thickness of about 0.0005-0.004 inches and a diameter of about 1.0 mm.-10.0 mm.

13. The sensing device of claim 12 wherein the material is stainless steel or a noble alloy selected from the group consisting of platinum, gold, palladium, iridium and ruthenium alloys and combinations thereof.

14. The sensing device of claim 1 wherein the microelectode brain-contact surface has a diameter of about 10-250 microns.

15. The sensing device of claim 14 wherein the microelectode sensing element is comprised of a noble alloy selected from the group consisting of platinum, gold, palladium, iridium and ruthenium alloys and combinations thereof.

* * * * *